United States Patent [19]

Suzuki

[11] Patent Number: 5,047,329

[45] Date of Patent: Sep. 10, 1991

[54] METHOD FOR THE MEASUREMENT OF CREATINE OR CREATININE AND REAGENTS FOR THESE MEASUREMENTS

[75] Inventor: Masaru Suzuki, Kashiwa, Japan

[73] Assignee: Noda Institute for Scientific Research, Noda, Japan

[21] Appl. No.: 141,043

[22] Filed: Jan. 5, 1988

[30] Foreign Application Priority Data

Jan. 23, 1987 [JP] Japan .................................. 62-13645

[51] Int. Cl.$^5$ ............................................. C12Q 1/34
[52] U.S. Cl. ..................................... 435/18; 435/25; 435/28; 435/805; 436/175; 422/56; 422/57; 422/58
[58] Field of Search ...................... 435/25, 18, 28, 805; 436/175; 422/56, 57, 58

[56] References Cited

U.S. PATENT DOCUMENTS

| | | | |
|---|---|---|---|
| 3,806,416 | 4/1974 | Mollering et al. | 195/62 |
| 3,806,420 | 4/1974 | Holz et al. | 195/66 |
| 3,907,644 | 9/1975 | Mollering et al. | 195/99 |
| 3,912,588 | 10/1975 | Mollering et al. | 195/29 |
| 4,039,384 | 8/1977 | Suzuki et al. | 195/62 |
| 4,812,399 | 3/1989 | Mauck et al. | 435/18 |

OTHER PUBLICATIONS

Suzuki, Chem. Abstracts, 94(13): 98557a, 1981, Purification and Some Properties of Sarcosine Oxidase from Corynebacterium sp. U-96.

Roberts et al., J. Biol. Chem., Nov. 5, 1985, 260 (25) pp. 13502–13508, Higher Homolog and N-Ethyl Analog of Creatine as Synthetic Phosphagen Precursors in Brain, Heart, and Muscle, Repressors of Liver Amidinotransferase, and Substrates for Creatine Catabolic Enzymes.

Chem. Abstracts, 92:210988d, 1980, Danninger et al., Method and Reagent for Carrying out Enzymatic Determinations Clinical Chemistry, vol. 33, No. 6, 1987, Bissell et al., Multilaboratory Evaluation of the New, Single-Slide Enzymatic Creatinine Method on the Kodak Ektachem Analyzer.

Kopper, Arch. Biochem, Vol. 19, pp. 171–172 (1949).

Roche, Biochem, Biophys. Acta. vol. 6, pp. 210–216 (1950).

Miller, J. Biol. Chem. vol. 121, pp. 457–464 (1937).

Dubos, J. Biol. Chem. vol. 121, pp. 429–445 (1937).

Tanzer, J. Biol. Chemistry, vol. 234, pp. 3201–3204 (1959).

Appleyard, J. Gen. Microbiology, vol. 14, pp. 351–365 (1956).

Kopper, J. Bacteriology, vol. 54, pp. 359–362 (1947).

Van Eyk, Enzymologie, vol. 34, pp. 198–202 (1968).

Kaplan, Molecular & Cellular Biochemistry, vol. 3, pp. 9–15 (1975).

Kopper, Archives of Biochem. & Biophys. vol. 15, pp. 195–199 (1947).

*Primary Examiner*—Christine Nucker
*Assistant Examiner*—Laurie Scheiner
*Attorney, Agent, or Firm*—Banner, Birch, McKie & Beckett

[57] ABSTRACT

A method for measuring creatine in a sample by the use of creatine amidinohydrolase which comprises decomposing the N-ethylglycine present in the sample enzymatically and thereafter reacting sarcosine oxidase upon the sample; and a reagent for use in the measurement of creatine comprising the first reagent and the second reagent, wherein the first reagent comprises a sarcosine oxidase of which Km value to N-ethylglycine at pH 8, 37° C. is 20 mM or below and catalase or comprises said sarcosine oxidase, a hydrogen donor oxidatively condensable with 4-aminoantipyrine and peroxidase and the second reagent comprises creatine amidinohydrolase, a sarcosin oxidase of which Km value to N-ethylglycine at pH 8, 37° C. is 50 mM or above, peroxidase and a color reagent for $H_2O_2$.

8 Claims, No Drawings

METHOD FOR THE MEASUREMENT OF CREATINE OR CREATININE AND REAGENTS FOR THESE MEASUREMENTS

BACKGROUND OF THE INVENTION

1. Field of the Invention

The present invention relates to an enzymatic method for measuring creatine or creatinine in serum, as well as to a reagent for use in these measurements.

2. Description of the Prior Art

Today, the measurement of creatine or creatinine in serum and urine is an important item of clinical test for diseases of kidney and muscles. In most cases, the measurement is carried out according to the Jaffe method. This method is based on a non-specific chemical reaction and the results obtained by this method can be erroneous. A variety of enzymatic methods have recently been developed with the aim of overcoming this disadvantage of Jaffe method, of which one example is a color-forming determination by the following enzymatic reactions (Japanese Patent Publication No. 60-3480):

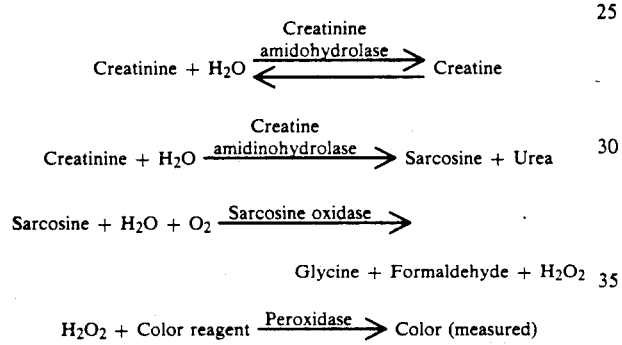

The above-mentioned method is advantageous in that it is not influenced by various substances affecting Jaffe method such as protein, ketone compound, cephalosporin type antibiotics, etc. However, this method is disadvantageous in that it makes a plus error (abnormally high result of measurement) because sarcosine oxidase acts not only upon sarcosine but also upon N-ethylglycine which is a metabolic product of therapeutically administered drug (e.g. lidocaine) owing to its substrate specificity. The present inventors conducted many studies with the aim of overcoming the disadvantage of the prior enzymatic measurement to find that creatine or creatinine in a sample can be determined with a high accuracy if N-ethylglycine present in the sample is previously decomposed with an enzyme exhibiting a high activity on N-ethylglycine and thereafter the creatine or creatinine is measured. Based on this finding, the present invention was accomplished.

SUMMARY OF THE INVENTION

The present invention provides the following methods and reagents:

(1) A method for measuring creatine in a sample by the use of creatine amidinohydrolase which comprises enzymatically decomposing the N-ethylglycine present in the sample and thereafter making sarcosine oxidase act upon the sample.

(2) A method according to item (1), wherein, in measuring creatine in a sample by the use of creatine amidinohydrolase, the N-ethylglycine present in the sample is previously decomposed with a sarcosine oxidase of which Km value (Michaelis constant) to N-ethylglycine is 20 mM or below and thereafter the creatine is measured by adding a sarcosine oxidase of which Km value (Michaelis constant) to N-ethylglycine is 50 mM or above or making it act separately.

(3) A method for measuring creatinine in a sample by the use of creatinine amdohydrolase and creatine amidinohydrolase which comprises enzymatically decomposing the N-ethylglycine present in the sample and thereafter making sarcosine oxidase act upon the sample.

(4) A process according to item (3), wherein, in measuring creatinine in a sample by the use of creatinine amidohydrolase and creatine amidinohydrolase, the N-ethylglycine present in the sample is decomposed with a sarcosine oxidase of which Km value (Michaelis constant) to N-ethylglycine is 20 mM or below and thereafter creatinine is measured by adding a sarcosine oxidase of which Km value to N-ethylglycine is 50 mM or above or making the sarcosine oxidase act upon the sample separately.

(5) A reagent for use in the measurement of creatine comprising the first reagent and the second reagent, wherein the first reagent comprises a sarcosine oxidase of which Km value to N-ethylglycine is 20 mM or below at pH 8, 37° C. and catalase or comprises the abovementioned sarcosine oxidase, a hydrogen donor oxidatively condensable with 4-aminoantipyrine and peroxidase and the second reagent comprises creatine amidinohydrolase, a sarcosine oxidase of which Km value to N-ethylglycine is 50 mM or above at pH 8, 37° C., peroxidase and a color reagent for $H_2O_2$.

(6) A reagent for use in the measurement of creatinine comprising the first reagent and the second reagent, wherein the first reagent comprises creatine amidinohydrolase, a sarcosine oxidase of which Km value to N-ethylglycine is 20 mM or below at pH 8, 37° C. and catalase or comprises the same creatine amidinohydrolase and sarcosine oxidase as above, a hydrogen donor oxidatively condensable with 4-aminoantipyrine and peroxidase and the second reagent comprises creatinine amidohydrolase, a sarcosine oxidase of which Km value to N-ethylglycine is 50 mM or above at pH 8, 37° C., peroxidase and a color reagent for $H_2O_2$.

DETAILED DESCRIPTION OF THE INVENTION

Hereunder, the invention will be explained concretely.

First, the test liquid of the present invention may be any samples such as serum, urine and the like.

I. Measurement of Creatine

The first reaction:

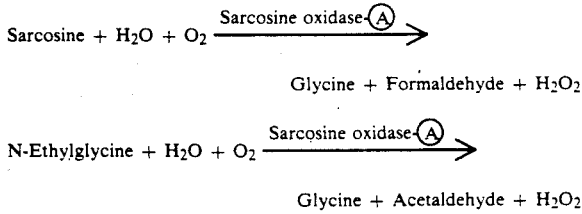

-continued

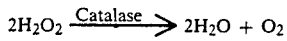

or

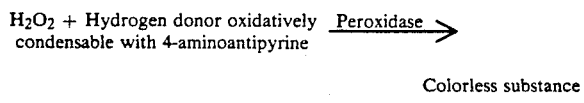

The second reaction:

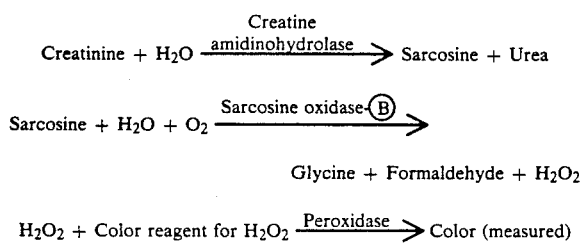

All these reactions are preferably carried out at a pH value of 6.5 to 9.0. The hydrogen donors oxidatively condensable with 4-aminoantipyrine include the followings:

(i) phenolic compounds represented by the following general formula (I):

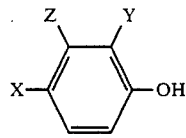

wherein X represents a halogen atom; Y represents a hydrogen atom, a halogen atom, a lower alkyl group or a lower alkoxyl group; and Z represents a hydrogen atom, a sulfonic acid group or a carboxyl group;

(ii) aniline derivatives represented by the following general formula (II):

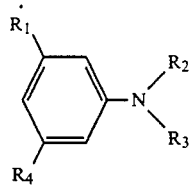

wherein $R_1$ and $R_4$ each represents a hydrogen atom, a lower alkyl group or a lower alkoxyl group; and $R_2$ and $R_3$ each represents a lower alkyl group, a hydroxy-(lower alkyl) group, an acetylamido-containing lower alkyl group or a sulfonic acid group-containing lower alkyl group;

(iii) toluidine derivatives; and
(iv) anisidine derivatives.

Examples of the phenolic compound represented by general formula (I) include p-chlorophenol, p-bromophenol, 2,4-dichlorophenol, 2,4-dibromophenol, 2,4-dichlorophenol sulfonate and the like.

Examples of the aniline derivative represented by general formula (II) include diethylaniline, N,N-diethyl-m-toluidine, m-methoxy-N,N-dimethylaniline, N-ethyl-N-(3-methylphenyl)-N-acetylethylenediamine, sodium-N-ethyl-N-(3-sulfopropyl)-m-toluidine, sodium-N-ethyl-N-(2-hydroxy-3-sulfopropyl)-3,5-dimethoxyaniline, and the like.

Examples of said toluidine derivative include N,N-dimethyl-m-toluidine, N,N-diethyl-m-toluidine, N,N-diethanol-m-toluidine, 3-methyl-N-ethyl-N'-hydroxyethylaniline, N-ethyl-N-(3-methylphenyl)-N'-acetylethylenediamine, N-ethyl-N-(3-methylphenyl)-N-succinylethylenediamine, N-(3-methylsulfonamidoethyl)-m-toluidine, N-methyl-N-(3-sulfopropyl)-m-toluidine, sodium-N-ethyl-N(2-hydroxy-3-sulfopropyl)-m-toluidine, sodium-3,5-dimethyl-N-ethyl-N-(2-hydroxy-3-sulfopropyl)-aniline, and the like.

Examples of said anisidine derivative include N,N-dimethyl-m-methoxy-aniline, sodium-N-ethyl-N-(2-hydroxy-3-sulfopropyl)-m-anisidine, sodium-N-(2-hydroxy-3-sulfopropyl)-3,5-dimethoxyaniline, m-acetamido-N,N-diethylaniline, and the like.

The color reagent for $H_2O_2$ usable in the present invention includes the followings:

(i) a combination of 4-aminoantipyrine and a phenolic compound represented by the following general formula (I):

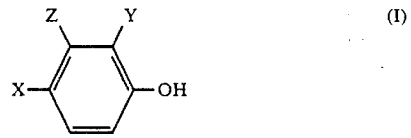

wherein X represents a halogen atom; Y represents a hydrogen atom, a halogen atom, a lower alkyl group or a lower alkoxyl group; and Z represents a hydrogen atom, a sulfonic acid group or a carboxyl group;

(ii) a combination of 4-aminoantipyrine and an aniline derivative represented by the following general formula (II):

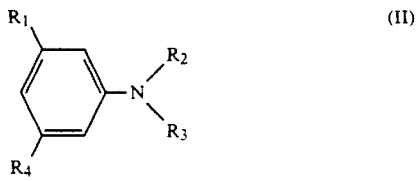

wherein $R_1$ and $R_4$ each represents a hydrogen atom, a lower alkyl group or a lower alkoxyl group; $R_2$ and $R_3$ each represents a lower alkyl group, a hydroxy-(lower alkyl) group, an acetylamido-containing lower alkyl group or a sulfonic acid group-containing lower alkyl group;

(iii) combination of 4-aminoantipyrine and a toluidine derivative;
(iv) a combination of 4-aminoantipyrine and an anisidine derivative; and
(v) a combination of diethylaniline or dimethylaniline and 3-methyl-2-benzothiazolinonehydrazone.

Examples of the phenolic compound represented by general formula (I) include p-chlorophenol, p-bromophenol, 2,4-dichlorophenol, 2,4-dibromophenol, 2,4-dichlorophenol sulfonate, and the like.

Examples of the aniline derivative represented by general formula (II) include diethylaniline, N,N-diethyl-m-toluidine, m-methoxy-N,N-dimethylaniline, N-ethyl-N-(3-methylphenyl)-N-acetylethylenediamine, sodium-N-ethyl-N-(3-sulfopropyl)-m-toluidine, sodium- N-ethyl-N-(2-hydroxy-3-sulfopropyl)-3,5-dimethoxyaniline, and the like.

Examples of the toluidine derivative include N,N-dimethyl-m-toluidine, N,N-diethyl-m-toluidine, N,N-diethanol-m-toluidine, 3-methyl-N-ethyl-N'-hydroxyethylaniline, N-ethyl-N-(3-methylphenyl)-N'-acetylethyl-enediamine, N-ethyl-N-(3-methylphenyl)-N-(3-methylphenyl)-N-succinylethylene-diamine, N-(3-methylsulfonamidoethyl)-m-toluidine, N-methyl-N-(3-sulfopropyl)-m-toluidine, sodium-N-ethyl-N-(2-hydroxy-3-sulfopropyl)-m-toluidine, sodium-3,5-dimethyl-N-ethyl-N-(2-hydroxy-3-sulfopropyl)-aniline, and the like.

Examples of the anisidine derivative include N,N-dimethyl-m-methoxy-aniline, sodium-N-ethyl-N-(2-hydroxy-3-sulfopropyl)-m-anisidine, sodium-N-(2-hydroxy-3-sulfopropyl)-3,5-dimethoxyaniline, m-acetamido-N,N-diethylaniline, and the like.

According to the present invention, ascorbic acid present in a sample which disturbs the color formation from hydrogen peroxide can be removed by reacting ascorbic acid oxidase upon it. The ascorbic acid oxidase may be reacted either prior to other enzymatic reactions or in conjugation and simultaneously with other enzymatic reactions. As the ascorbic acid oxidase, those from plants are used, among which those from pumpkin and cucumber are preferable.

The sarcosine oxidase-(A) used herein may be of any origins, so far as it exhibits a high activity upon N-ethylglycine and its Km value (Michaelis constant) to N-ethylglycine is 20 mM or below. Sarcosine oxidases satisfying the above-mentioned conditions include those produced by the microorganisms belonging to, for example, Genus Corynebacterium, Genus Arthrobacter, Genus Alcaligenes, Genus Pseudomonas, Genus Micrococcus, etc. All these enzymes can be produced by a cuture and are available commercially. The sarcosine oxidase-(B) used herein may be of any origins, so far as it has a low activity upon N-ethylglycine and its Km value (Michaelis constant) to N-ethylglycine is 50 mM or above and it has a high activity upon sarcosine. Its preferable examples are the sarcosine oxidases produced by Genus Bacillus and particularly sarcosine oxidase-N (Japanese Patent Application Kakai (Laid-Open) No. 61-162,174 which corresponds to U.S. Pat. No. 4,740,465).

II. Measurement of Creatinine

The first reaction:

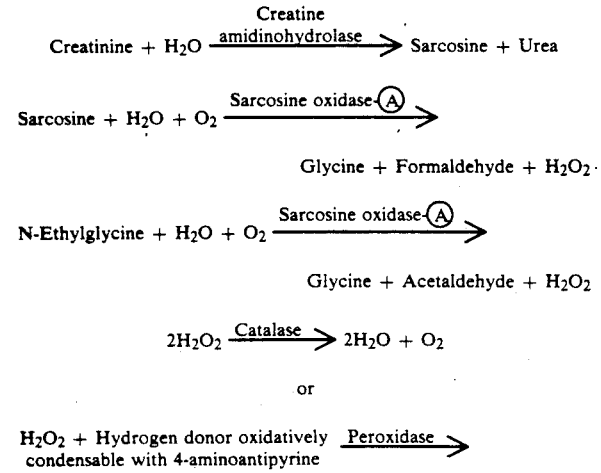

The second reaction:

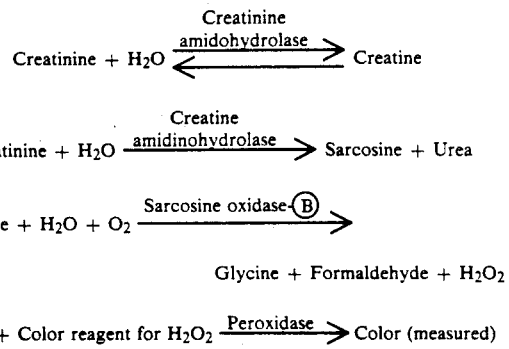

As the hydrogen donor oxidatively condensable with 4-aminoantipyrine and the color reagent for $H_2O_2$ used herein, the same ones as used in the aforementioned measurement of creatine can be used.

The enzymes used in the present invention may be any origins. As for the creatinine amidohydrolase and creatine amidinohydrolase, all the enzymes conventionally used in the measurements of creatinine and creatine can be used without exception. Thus, examples of the creatinine amidohydrolase include the creatinine amidohydrolases produced by the microorganisms belonging to Genus Alcaligenes, Genus Penicillium, Genus Pseudomonas, Genus Flavobacterium, Genus Arthrobacter, Genus Corynebacterium, etc., and examples of the creatine amidinohydrolase include the creatine amidinohydrolases produced by the microorganisms belonging to Genus Pseudomonas, Genus Bacillus, Genus Alcaligenes, Genus Flavabacterium, Genus Arthrobacter, Genus Corynebacterium, etc. As the catalase and peroxidase, any of those from animals and those from vegetables can be used. All these enzymes can be produced by a culture and are available commercially.

According to the present invention, the analysis of creatine or creatinine is carried out in liquid or dry state. When it is carried out in liquid state, the above-mentioned first reagent and sample are mixed together and the substances to be removed (for example, sarcosine, N-ethylglycine, etc.) are enzymatically decomposed at 37° C., after which the second reagent is added and the hydrogen peroxide formed from creatine or creatinine present in the sample is converted to a color by the reaction between peroxidase and the color reagent for hydrogen peroxide and then the color is measured by means of spectrophotometer. When the analysis is carried out in dry state, the first and second reagents are separately absorbed into and coated onto an absorbent carrier such as filter paper, strip, gelatin film or the like, and a molecular fractionation film made of polyacrylamide or the like is inserted between the two absorbent carriers. By means of a supporting film, the multilayer product thus obtained is mounted on a transparent material through which analysis can be performed by means of spectrophotometer. Then, a sample solution is dropped onto the multi-layer surface and the extent of coloration formed by reaction is measured, from which creatine or creatinine is determined.

According to the present invention, N-ethylglycine present in a sample is decomposed by the use of an enzyme having a high activity upon N-ethylglycine (i.e.

sarcosine oxidase) and thereafter creatine or creatinine is measured. Accordingly, the creatine or creatinine in the sample can be measured with a very high accuracy. Thus, the method of the present invention has a very high significance in the clinical tests for diagnoses.

Next, the present invention will be explained more concretely with reference to the following examples.

EXAMPLE 1

The First Reagent: It was prepared by dissolving 40 KU (kilo unit) of creatine amidinohydrolase (manufactured by Seishin Pharmaceutical Co., Ltd.), 3 KU of sarcosine oxidase (manufactured by Seishin Pharmaceutical Co., Ltd., Km value to N-ethylglycine: 11 mM), 7 KU of peroxidase from horseradish, 0.5 KU of ascorbic acid oxidase, 0.5 mM of 2,4-dichlorophenol sulfonate, 200 mg of EDTA.2Na and 0.4 g of Triton X-100 into 100 ml of 0.1 TES Good buffer (pH 8.0).

The Second Reagent: It was prepared by dissolving 10 KU of creatinine amidohydrolase (manufactured by Seishin Pharmaceutical Co., Ltd.), 1 KU of sarcosine oxidase N (prepared according to the method mentioned in Japanese Patent Application Kokai (laid-Open) No. 61-162,174 which corresponds to U.S. Pat. No. 4,740,465), Km value of N-ethylglycine: 77 mM), 1.7 mg of potassium ferrocyanide, 0.15 mM of 2,4-dichlorophenol sulfonate, 0.05 mM of 4-aminoantipyrine, 200 mg of EDTA.2Na and 0.4 g of Triton X-100 into 100 ml of 0.1 TES Good buffer (pH 8.0).

Sample (human serum, 0.1 ml) was taken, and it was mixed and reacted with 0.1 ml of the first reagent at 37° C. for 5 minutes to decompose creatine, sarcosine and N-ethylglycine present in the sample. Then, 1.5 ml of the second reagent was added and reacted at 37° C. for 5 minutes. By means of Microspectrometer (Stasar III manufactured by Corning Medical Co., Ltd.), O. D. value (optical density) was measured at 510 nm, from which the quantity of creatinine was determined with reference to a calibration curve having previously been prepared from authentic creatinine sample of known concentration.

On the other hand, for comparison, 0.9 mg/dl of N-ethylglycine was added to a human serum containing 1.00 mg/dl of creatinine (a standard human serum to which 1.00 mg/dl of standard creatinine had been added), and creatinine was measured by the method of the present invention and the prior method. In the prior method, a mixture of the first and second reagnets was reacted upon the sample at 37° C. for 10 minutes without carrying out the decomposition of N-ethylglycine, provided that no catalase was used. As the result, the method of the present invention gave a result of 0.99 mg/dl, while the prior method gave a result of 1.81 mg/dl.

EXAMPLE 2

The First Reagent: It was prepared by dissolving 3 KU of sarcosine oxidase (manufactured by Seishin Pharmaceutical Co., Ltd., Km value to N-ethylglycine: 11 mM), 7 KU of peroxidase from horseradish (manufactured by Toyobo Co., Ltd.), 0.5 KU of ascorbic acid oxidase (manufactured by Toyobo Co., Ltd.), 0.5 mM of 2,4-dichlorophenol sulfonate, 200 mg of EDTA.2Na and 0.4 g of Triton X-100 into 100 ml of 0.1 M TES Good buffer (pH 8).

The Second Reagent: It was prepared by dissolving 3 KU of creatine amidinohydrolase, 1 KU of the same sarcosine oxidase N as in Example 1, 1.7 mg of potassium ferrocyanide, 0.15 mM of 2,4-dichlorophenol sulfonate, 0.05 mM of 4-aminoantipyrine, 200 mg of EDTA.2Na and 0.4 g of Triton X-100 into 100 ml of 0.1 M TES Good buffer (pH 8).

Sample (human serum, 0.1 ml) was taken, and it was mixed with 0.1 ml of the first reagent and reacted at 37° C. for 5 minutes to decompose the sarcosine and N-ethylglycine present in the sample. Then, 1.5 ml of the second reagent was added and reacted at 37° C. for 5 minutes. By means of Microspectrophotometer (Stasar III manufactured by Corning Medical Co., Ltd.), O. D. value was measured at 510 nm, from which the quantity of creatine was determined with reference to a calibration curve having previously been prepared from authentic creatine sample.

On the other hand, for comparison, 0.9 mg/dl of N-ethylglycine was added to a human serum containing 1.00 mg/dl of creatine (a standard human serum to which 1.00 mg/dl of standard creatine had been added), and the quantity of creatine was determined by the method of the present invention and the prior method. As the result, the method of the invention gave a result of 1.01 mg/dl, while the prior method gave a result of 1.84 mg/dl.

It is apparent from the examples presented above that, according to the method of the present invention, the reaction progresses specifically and therefore creatine and creatinine can be determined with a higher accuracy than in the prior method.

What is claimed is:

1. A method for measuring creatine in a sample comprising: decomposing N-ethylglycine present in the sample enzymatically with sarcosine oxidase of which Km value (Michaelis constant) to N-ethylglycine at pH 8, 37° C. is 20 mM or below and thereafter determining creatine by reacting the decomposed sample with creatine amidinohydrolase and sarcosine oxidase N of which Km value (Michaelis constant) to N-ethylglycine at pH 8, 37° C. is 50 mM or above as obtained by culturing Bacillus sp. NS-129 (FERM BP-671) and measuring final reaction products as a measure of creatine present in the sample.

2. A method for measuring creatinine in a sample comprising decomposing creatine and N-ethylglycine present in the sample enzymatically with creatine amidinohydrolase and sarcosine oxidase of which Km value (Michaelis constant) to N-ethylglycine at pH 8, 37° C. is 20 mM or below, and thereafter determining creathinine by reacting the decomposed sample with creatinine amidinohydrolase and sarcosine oxidase N of which Km value (Michaelis constant) to N-ethylglycine at pH 8, 37° C. is 50 mM or above as obtained by culturing Bacillus sp. NS-129 (FERM BP-671) and measuring final reaction products as a measure of creatinine present in the sample.

3. A reagent for use in the measurement of creatine comprising the first reagent and the second reagent, wherein the first reagent comprises a sarcosine oxidase of which Km value to N-ethylglycine at pH 8, 37° C. is 20 mM or below and catalase or comprises the same sarcosine oxidase as above, a hydrogen donor oxidatively condensable with 4-aminoantipyrine and peroxidase and the second reagent comprises creatine amidinohydrolase, sarcosine oxidase N of which Km value to N-ethylglycine at pH 8, 37° C. is 50 mM or above as obtained by culturing Bacillus sp. NS-129 (FERM BP-671) peroxidase and a color reagent for $H_2O_2$.

4. A reagent for use in the measurement of creatinine comprising the first reagent and the second reagent, wherein the first reagent comprises creatine amidinohydrolasee, a sarconsine oxidase of which Km value to N-ethylglycine at pH 8, 37° C. is 20 mM or below and catalase or comprises the same creatine amidinohydrolase and sarcosine oxidase as above, a hydrogen donor oxidatively condensable with 4-aminoantipyrine and peroxidase and the second reagent comprises creatinine amidohydrolase, sarcosine oxidase N of which Km value to N-ethylglycine at pH 8, 37° C. is 50 mM or above as obtained by culturing Bacillus sp. NS-129 (FERM BP-671) peroxidase and a color reagent for $H_2O_2$.

5. A method according to claim 1 wherein the measuring of creatine is carried out in liquid state or dry state.

6. A method according to claim 2 wherein the measuring of creatinine is carried out in liquid or dry state.

7. A method according to claim 5 wherein the measuring is carried out in the dry state.

8. A method according to claim 6 wherein the measuring is carried out in the dry state.

* * * * *